(12) United States Patent
Beldjoudi et al.

(10) Patent No.: US 9,476,923 B2
(45) Date of Patent: Oct. 25, 2016

(54) METHOD AND DEVICE FOR IDENTIFYING A MATERIAL BY THE SPECTRAL ANALYSIS OF ELECTROMAGNETIC RADIATION PASSING THROUGH SAID MATERIAL

(75) Inventors: Guillaume Beldjoudi, Grigny (FR); Veronique Rebuffel, Corenc (FR); Jean Rinkel, Bures-sur-Yvette (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 152 days.

(21) Appl. No.: 14/130,221
(22) PCT Filed: Jun. 29, 2012
(86) PCT No.: PCT/FR2012/051510
§ 371 (c)(1),
(2), (4) Date: Dec. 30, 2013
(87) PCT Pub. No.: WO2013/001247
PCT Pub. Date: Jan. 3, 2013

(65) Prior Publication Data
US 2014/0126693 A1 May 8, 2014

(30) Foreign Application Priority Data

Jun. 30, 2011 (FR) ...................................... 11 02070

(51) Int. Cl.
*G01N 23/087* (2006.01)
*G01B 15/02* (2006.01)
(Continued)

(52) U.S. Cl.
CPC ............. *G01R 23/18* (2013.01); *G01B 15/025* (2013.01); *G01N 23/087* (2013.01); *G01R 23/16* (2013.01); *G06K 9/00523* (2013.01); *A61B 6/52* (2013.01); *G01N 2223/3037* (2013.01)

(58) Field of Classification Search
CPC .... G01B 15/00; G01B 15/02; G01B 15/025; G01N 23/00; G01N 23/02; G01N 23/06; G01N 23/08; G01N 23/083; G01N 23/087; G06K 9/00496; G06K 9/00523; G01R 23/00; G01R 23/16; G01R 23/18; A61B 6/52; A61B 6/5205; A61B 6/5294
USPC ...... 378/51, 53, 56, 91, 98.9, 162, 165, 207, 378/210
See application file for complete search history.

(56) References Cited

U.S. PATENT DOCUMENTS 6,018,562 A * 1/2000 Willson ............... G01N 23/087
378/57
6,441,375 B1 8/2002 Joseph et al.
(Continued)

FOREIGN PATENT DOCUMENTS

FR 2 953 603 6/2011
WO 01 50112 7/2001

OTHER PUBLICATIONS

Meyer, K. et al., "Qualitative and quantitative mixture analysis by library search: infrared analysis of mixtures of carbohydrates", Analytica Chimica Acta, vol. 281, No. 1, pp. 161-171, (Sep. 1, 1993) XP026592982.

(Continued)

*Primary Examiner* — Anastasia Midkiff
(74) *Attorney, Agent, or Firm* — Oblon, McClelland, Maier & Neustadt, L.L.P.

(57) ABSTRACT

A method identifying a material, includes: measuring an electromagnetic radiation spectrum emitted through the material; determining at least one measurement energy band, and spectral coefficients of a comparison function in the measurement band, using the measured spectrum; estimating, using the determined spectral coefficients, a nature and/or thickness of the material based on a set of reference spectral parameters relating to reference materials and/or thicknesses and defined in reference bands. The estimating includes: prior selecting plural reference materials and/or thicknesses, as possible candidates, from comparing the spectral coefficients determined with at least one portion of the reference spectral parameters; estimating the nature and/or thickness of the material from comparing the spectral coefficients determined with the spectral parameters of at least one portion of the possible candidates, in at least one energy band common to the reference bands of the at least one portion of possible candidates and the measurement band.

14 Claims, 4 Drawing Sheets

(51) Int. Cl.
    *G01R 23/18*    (2006.01)
    *G01R 23/16*    (2006.01)
    *G06K 9/00*     (2006.01)
    *A61B 6/00*     (2006.01)

(56) References Cited

U.S. PATENT DOCUMENTS

| | | |
|---|---|---|
| 2007/0108379 A1 | 5/2007 | Rowland et al. |
| 2008/0298544 A1 | 12/2008 | Dugan |
| 2009/0003651 A1 | 1/2009 | Dugan et al. |
| 2009/0003699 A1 | 1/2009 | Dugan et al. |
| 2009/0052622 A1 | 2/2009 | Dugan et al. |
| 2009/0052732 A1 | 2/2009 | Dugan et al. |
| 2009/0052762 A1 | 2/2009 | Dugan et al. |
| 2009/0055344 A1 | 2/2009 | Dugan et al. |
| 2010/0220835 A1* | 9/2010 | Gibson ............... G01V 5/0016 378/53 |
| 2011/0249788 A1* | 10/2011 | Nuesch ............... G01N 23/046 378/53 |
| 2012/0116691 A1* | 5/2012 | Joyce .................. G01N 23/10 702/28 |
| 2012/0239310 A1 | 9/2012 | Ouvrier-Buffet et al. |

OTHER PUBLICATIONS

International Search Report Issued Oct. 25, 2012 in PCT/FR12/051510 Filed Jun. 29, 2012.

* cited by examiner

METHOD AND DEVICE FOR IDENTIFYING A MATERIAL BY THE SPECTRAL ANALYSIS OF ELECTROMAGNETIC RADIATION PASSING THROUGH SAID MATERIAL

This invention relates to a method for identifying a material by spectral analysis of electromagnetic radiation able to pass through this material. It further relates to a corresponding device and computer program.

It relates among others to the fields of spectral analysis by X and gamma rays. This analysis is for example used in non-destructive testing applications, in particular continuously running luggage inspection by radiography for detecting explosive materials in airports. The application for continuously running luggage inspection is in particular highly demanding in terms of rapidity (the continuously running speed of the luggage imposes taking a measurement of the energy of the photons transmitted through the luggage over a generally short period of time, a few ms, with an incident flow of photons that can be high, a few tens of Mphotons/mm$^2$/s, in order to retain a sufficient statistic), precision and reliability (for obvious reasons of security).

The invention applies more particularly to a method for identifying comprising the following steps:
- measuring a spectrum of electromagnetic radiation emitted through the material to be identified,
- determining at least one energy band, referred to as a measurement band, and spectral coefficients of a comparison function in this measurement band, using the measured spectrum,
- estimating, using the determined spectral coefficients, the nature and/or the thickness of the material to be identified on the basis of a set of reference spectral parameters relating to reference materials and/or thicknesses, these reference spectral parameters being defined for each reference material and/or thickness in at least one energy band referred to as a reference band.

Generally, "spectrum" of an electromagnetic radiation means a set of values of the intensity of this electromagnetic radiation according to the photon energy.

"Comparison function" linked to a material to be identified means a function that compares, at a given energy or over at least one given energy band, the intensity of the electromagnetic radiation transmitted by the material to the intensity of the incident electromagnetic radiation to the material.

More precisely, this comparison is generally carried out by a ratio, such that the comparison function is obtained by carrying out, at a given energy or over at least one given energy band, a ratio between the intensity of the radiation transmitted and the intensity of the incident radiation.

Therefore, if $I(E)$ and $I_0(E)$ designate respectively the number of photons transmitted by the material and the number of incident photons to the material per unit of time at the energy E or in the energy band E, the comparison function $TR(E)$ can take the following form:

$$TR(E) = \frac{I(E)}{I_0(E)}. \tag{1}$$

In this form, the comparison function can be designated by the term of transmission function.

Moreover, if $\mu(E)$ designates the linear attenuation coefficient of the material at the energy E or in the energy band E and if d designates the thickness of material passed through by the radiation, it is known that:

$$I(E) = I_0(E) e^{-\mu(E)d}.$$

As such, in order to obtain a comparison function linearly dependent on the linear attenuation coefficient of the material, it can be advantageous to express the transmission of the photons in the material by using the natural logarithm of the previously described ratio. In this case, the comparison function $TR(E)$ can take the following form:

$$TR(E) = -\ln\left(\frac{I(E)}{I_0(E)}\right). \tag{2}$$

In this form, the comparison function is usually designated by the term of attenuation function.

Consequently, in this patent application, the term of comparison function covers both:
- a transmission function obtained using a ratio between the intensity of the radiation transmitted by the material and the intensity of the incident radiation to the material at a given energy or over at least one given energy band, such as for example that defined by the equation (1), and
- an attenuation function obtained using the natural logarithm of the ratio defined in the previous paragraph, such as for example that defined by the equation (2).

The magnitudes $I(E)$ and $I_0(E)$, which designate respectively the intensity of the radiation transmitted and the intensity of the incident radiation, were more precisely defined previously as flows representing respectively a number of photons transmitted by the material and a number of incident photons to the material per unit of time at the energy E or in the energy band E, but they can also be defined as fluence rates (number of photons per units of time and of surface) or as numbers of photons detected during a determined time. In the rest of the description, they shall be defined as flows. Of course, they must be homogeneous, i.e. represent a magnitude of the same type, so that the comparison function is without a unit.

The magnitudes $I(E)$ and $I_0(E)$ are concretely measured using a detection system located on the path of the electromagnetic radiation:
- in the presence of the material to be identified between the source of the emission of the radiation and the detection system for the estimation of $I(E)$, and
- in the absence of the material to be identified, or by calculation if the emission parameters of the source are known, for the estimation of $I_0(E)$.

A known detection system is for example constituted of several scintillating detectors that do not have a spectrometric function. Such detectors are superimposed one over the other, with interleaving filtering screens able to be placed between two successive detectors. Generally, two detectors are used according to the denomination "Sandwich sensors": the first detector is of low volume, in such a way that it mainly absorbs the low-energy photons, and the second detector, placed after the first on the path of the electromagnetic radiation, is of a more substantial volume, in such a way that it mainly absorbs the high-energy photons. As such, by using these first and second detectors, an intensity of a low-energy component and an intensity of a high-energy component of the electromagnetic radiation are measured respectively, with these two intensities forming two components of a spectrum of radiation. By carrying out this measurement in the presence and in the absence of the material to be identified, the measurement of a two-value comparison function is obtained, here two spectral transmission or attenuation coefficients on two energy bands forming the measurement band.

Another known and more recent detection system comprises for example a spectrometric detector, in particular for example X rays, making it possible to obtain the measurement of a spectrum over an entire energy range and therefore the determination of spectral coefficients of a comparison function over at least one portion of this energy range forming the measurement band.

Regardless of the detection system used, the measurement makes it possible as such to obtain a plurality of spectral coefficients of a comparison function in the measurement band.

Using the detection system, it is also known to proceed with a calibration by the determination of comparison functions for comparing reference objects, said reference objects differing from one another by the nature of their material and/or their thickness. Likewise for each reference object, of a given material and thickness, reference spectral parameters are as such obtained, in particular spectral reference transmission or attenuation coefficients, in at least one energy band referred to as a reference band specific to the considered reference object.

In order to estimate the nature and/or the thickness of the material to be identified, an immediate solution is to calculate, using for example a predetermined distance function, the reference spectral coefficients that are the closest to the spectral coefficients determined for the material to be identified. It is then considered that the material to be identified has the characteristics (nature of the material and/or thickness) of the closest reference object. More generally, estimating the nature and/or the thickness of the material to be identified is carried out by a comparison of the spectral coefficients determined by the measurement with the reference spectral parameters. It is therefore necessary for this to compare the coefficients with the reference parameters in shared energy bands. Then consider only the coefficients that correspond to energies that are common to the measurement band and to all of the reference bands, i.e. to the intersection of the measurement band and of all the reference bands.

The problem with this estimation is that it must as such be carried out in an energy range that is possibly very restrained, in so much as the measurement via spectrometry can result in an absence of photons transmitted in certain energy channels, rendering these channels unusable for the estimation. As in addition this problem arises both during the measurement concerning the material to be identified and during the calibration, the shared energy band that is exploited for the identification can be highly reduced. In particular, very thick reference objects are the most attenuating and therefore the most responsible for the restriction of the shared energy band, which renders thin materials more difficult to identify. Likewise, reference objects in materials such as iron or lead induce energy ranges that are restricted and make it difficult to identify thin thicknesses of light materials such as plastics.

Finally, a photon noise exists on the attenuation measurements in such a way that determining the shared energy range is not easy since it is subject to the variations of photon noise.

It can as such be desired to provide a method for identifying a material, by spectral analysis of electromagnetic radiation able to pass through this material, which makes it possible to overcome at least one portion of the aforementioned disadvantages and constraints.

A subject matter of the invention is thus a method for identifying a material by spectral analysis of electromagnetic radiation able to pass through this material, comprising the following steps:
measuring a spectrum of electromagnetic radiation transmitted through the material to be identified,
determining at least one energy band, referred to as a measurement band, and spectral coefficients of a comparison function in this measurement band, using the measured spectrum,
estimating, using the determined spectral coefficients, the nature and/or the thickness of the material to be identified on the basis of a set of reference spectral parameters relating to reference materials and/or thicknesses, these reference spectral parameters being defined for each reference material and/or thickness in at least one energy band referred to as a reference band,
wherein the estimating comprises at least the two following steps:
prior selecting of a plurality of reference materials and/or thicknesses, referred to as possible candidates, from a comparison of the spectral coefficients determined with at least one portion of the reference spectral parameters,
estimating the nature and/or the thickness of the material to be identified from a comparison of the spectral coefficients determined with the spectral parameters of at least one portion of the possible candidates, in at least one energy band that is common to the reference bands of said at least one portion of the possible candidates and to the measurement band.

As such, this estimation in at least two separate phases comprising a prior selection of possible candidates makes it possible to proceed to the final estimation of the nature and/or of the thickness of the material to be identified on the basis of a shared energy band that is more substantial (intersection of the measurement band and of the reference bands of the possible candidates) than in prior art (intersection of the measurement band and of all of the reference bands), while still providing during each phase to compare the spectral coefficients determined by the measurement with at least one portion of the reference spectral parameters. The reliability of the method for identifying is therefore improved.

Optionally, the prior selecting of the possible candidates is carried out:
either in at least one energy band that is common to all of the reference bands and to the measurement band,
or in at least one energy band that is common to a predetermined portion of the reference bands and to the measurement band.

Also optionally, the reference materials and/or thicknesses comprise a plurality of reference materials each with a plurality of reference thicknesses.

Also optionally, the estimation comprises the following steps, executed for each reference material:
selecting a plurality of reference thicknesses for this reference material, referred to as possible candidates, by comparison of the spectral coefficients determined with the reference spectral parameters in at least one energy band that is common to the reference bands of each reference thickness for this reference material and to the measurement band,
selecting two consecutive reference thicknesses for this reference material by comparison of the spectral coefficients determined with the spectral parameters of at least one portion of the possible candidates, in at least one energy band that is common to the reference bands of said at least one portion of possible candidates and to the measurement band, estimating an optimum thickness for this reference material by comparison of the spectral coefficients determined with spectral parameters interpolated using spectral parameters relating to the two consecutive reference thicknesses selected, in at least one energy band that is common to the reference bands of the two consecutive reference thicknesses selected and to the measurement band.

Also optionally, estimating the nature and/or the thickness of the material to be identified comprises the selecting of an optimum thickness, among all of the optimum thicknesses each associated with a reference material, on the basis of an optimization of a criterion evaluated in at least one energy band that is common to all of the energy bands wherein the optimum thicknesses were estimated.

Also optionally, the reference spectral parameters relating to reference materials and/or thicknesses are probability density statistical parameters, each reference material and/or thickness being thus associated with a probability density making it possible to calculate a probability of measuring spectral coefficients in the presence of this reference material and/or thickness in its reference band.

Also optionally, the comparison of the spectral coefficients determined with the reference spectral parameters relating to a reference material and/or thickness comprises the estimating of a value that takes the probability density of this reference material and/or thickness when the spectral coefficients determined are applied to it.

Also optionally, the comparison of the spectral coefficients determined with the reference spectral parameters relating to a reference material and/or thickness comprises the estimating of a conditional posterior probability of being in the presence of this reference material and/or thickness knowing the determined spectral coefficients, on the basis of the product of a conditional posterior probability of measuring the spectral coefficients determined in the presence of this reference material and/or thickness and of a prior probability of being in the presence of this reference material and/or thickness, by application of Bayes' theorem.

Another subject matter of the invention is a device for identifying a material by spectral analysis of electromagnetic radiation able to pass through this material, comprising:
  a transmitter of electromagnetic radiation,
  a device for measuring a spectrum of electromagnetic radiation transmitted through the material to be identified,
  a calculator programmed for:
    determining at least one energy band, referred to as a measurement band, and spectral coefficients of a comparison function in this measurement band, using the measured spectrum, and
    estimating, using the determined spectral coefficients, the nature and/or the thickness of the material to be identified on the basis of a set of reference spectral parameters relating to reference materials and/or thicknesses, these reference spectral parameters being defined for each reference material and/or thickness in at least one energy band referred to as a reference band,
wherein the calculator is more precisely programmed for:
  prior selecting of a plurality of reference materials and/or thicknesses, referred to as possible candidates, from a comparison of the spectral coefficients determined with at least one portion of the reference spectral parameters, estimating the nature and/or the thickness of the material to be identified from a comparison of the spectral coefficients determined with the spectral parameters of at least one portion of the possible candidates, in at least one energy band that is common to the reference bands of said at least one portion of the possible candidates and to the measurement band.

Finally, another subject matter of the invention is a computer program which can be downloaded from a communications network and/or recorded on a support that can be read by a computer and/or that can be executed by a processor, comprising instructions for the execution of the steps of a method for identifying a material according to the invention, when said program is executed on a computer.

The invention shall be better understood thanks to the following description, provided solely by way of example and made in reference to the annexed drawings wherein.

Figure 1:
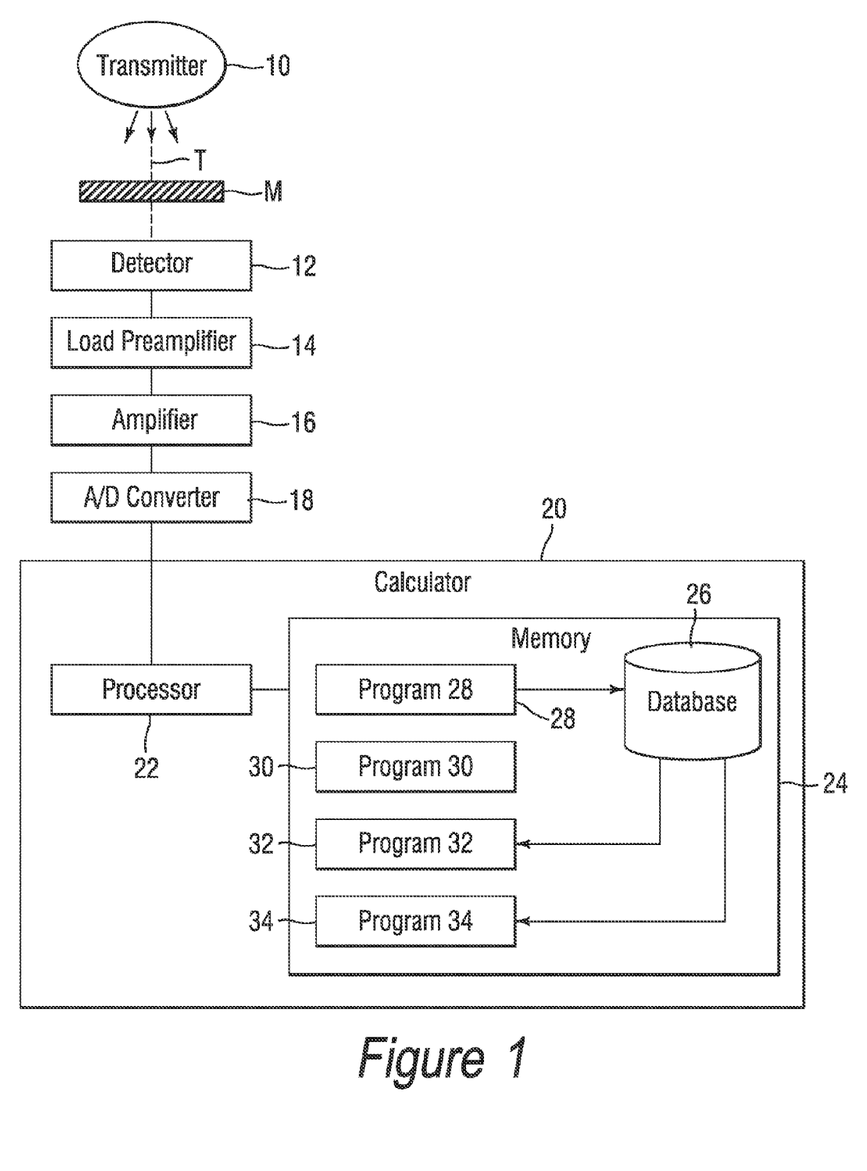
FIG. 1 diagrammatically shows the general structure of a device for identifying a material by spectral analysis of electromagnetic radiation able to pass through this material, according to an embodiment of the invention.

The device for identifying shown diagrammatically in FIG. 1 comprises a transmitter 10 of electromagnetic radiation, for example a source of X or gamma rays. If it is a source of X rays, the emitter 10 comprises for example a tungsten anode, a filter of 3 mm of aluminum and is powered with a voltage of 115 kV. The conventional parameters of intensity and of time are for example fixed in order to obtain a fluence of $7.8 \cdot 10^4$ photons/pixel.

On the path T of the radiation emitted, the device for identifying further comprises a detector 12, for example a spectrometric detector. This detector makes it possible to measure a spectrum of a radiation transmitted through a material to be identified M, with the latter being arranged between the emitter 10 and the detector 12 on the path T.

More precisely, the detector 12 is for example a direct conversion sensor, in particular made of semi-conductor material (CdTe, CdTe:Cl, CdTe:In, CdZnTe, CdMnTe, HgI2, AsGa, Si, TlBr, etc.). This sensor is provided with two electrodes at the terminals of which a pulse signal reveals an interaction of a radiation or of a photon with the material of the sensor and the creation of a cloud of electronic charges (typically of a magnitude from 10,000 electrons to a few tens of thousands of electrons for a photon X of 60 keV), in the material of the sensor, which results from this interaction. The charges are then captured by the two electrodes between which is established a required potential difference. If the collection is complete, the integral of the pulse measured is proportional to the energy deposited by the incident particle.

At the output of the spectrometric detector 12, the device for identifying further comprises a load preamplifier 14, an amplifier 16 and an analog to digital converter 18 for the supply of numerical values of the spectrum measured by the detector 12 to a calculator 20.

The calculator 20 is for example a conventional computer comprising a processor 22 associated with one or several memories identified by the generic reference 24. The memory 24 stores a database 26 of reference spectral parameters relating to reference materials and thicknesses, these reference spectral parameters being defined for each reference material and thickness in at least one energy band referred to as a reference band.

Figure 2:
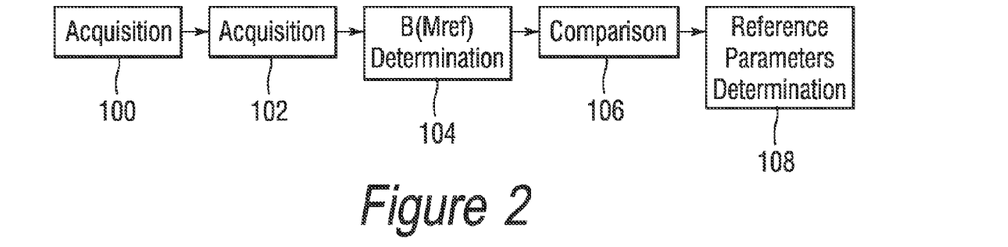
FIG. 2 shows the successive steps of a calibration method implemented by the device of FIG. 1, according to an embodiment of the invention.

The memory 24 further stores one or several computer programs 28, 30, 32, 34 constituted of sequences of instructions that make it possible, when they are executed by the processor 22, to carry out the following operations:

- calculating the reference spectral parameters of the database 26, during the implementation of a calibration method using a set of reference objects with known materials and thicknesses: this calibration method, of which details will be provided in reference to the FIG. 2, is implemented by the program 28,
- determining at least one energy band, referred to as a measurement band and spectral coefficients of a comparison function in this measurement band, using numerical values of a measured spectrum supplied to the calculator: this determination of the spectral coefficients in the measurement band is carried out by the program 30,
- selecting a plurality of reference objects, referred to as possible candidates, from a comparison of the spectral coefficients determined by the program 30 with at least one portion of the reference spectral parameters: this prior selecting is carried out in one or several iterations by the program 32, and
- estimating the nature and/or the thickness of the material to be identified from a comparison of the spectral coefficients determined by the program 30 with the spectral parameters of at least one portion of the possible candidates, in at least one energy band that is common to the reference bands of said at least one portion of the possible candidates and to the measurement band: this estimation is carried out by the program 34.

Figure 3:
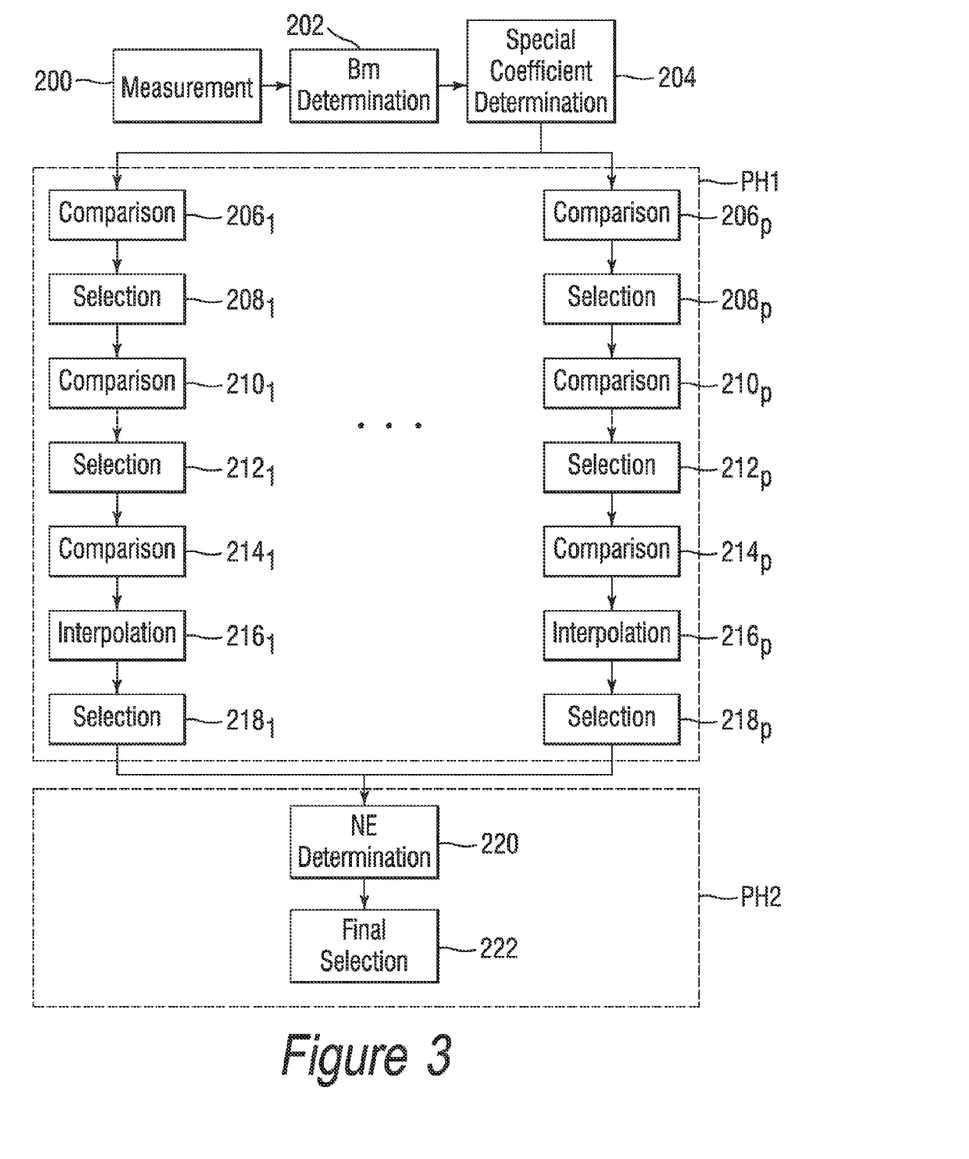
FIG. 3 shows the successive steps of a method for identifying implemented by the device of FIG. 1, according to a first embodiment of the invention.

Details on the method for identifying corresponding to the execution of the programs 30, 32 and 34 shall be provided in reference to FIG. 3, according to a possible embodiment of the invention.

Note moreover that the computer programs 28, 30, 32, 34 are presented as separate, but this distinction is purely functional. They could as well be grouped together into one or more pieces of software. Their functions could also be micro-programmed in dedicated integrated circuits.

The identification of an unknown material M consists in determining for example the nature of this material and its thickness from a comparison of the spectral coefficients coming from a measurement of this unknown material with the reference spectral parameters of the database 26 concerning the reference objects. According to different possible embodiments, the reference spectral parameters can be spectral coefficients that can be compared directly with spectral coefficients measured for the unknown material M or statistical parameters concerning such coefficients, in particular probability density parameters. As such, in the first case, the comparison can consist of a comparison of the coefficients measured with the reference spectral coefficients, in particular by a distance calculation. In the second case, the comparison can consist in searching for a maximum, for example among the values that take the reference probability densities at the values measured or among probabilities that are explicitly calculated, via Bayesian inference in particular, on the basis of the values measured. In any case, the comparison comes down to the optimization of a cost function, with the latter configured by the reference spectral parameters and being evaluated at the values taken by the spectral coefficients coming from the measurement.

The reference spectral parameters can a priori be known and stored in the database 26. They can also be obtained via a succession of measurements and calculations shown in FIG. 2.

Determination of the Reference Spectral Parameters

The calibration method shown in this figure comprises a first step 100 of acquiring spectrums without any object being arranged between the emitter 10 and the detector 12. This acquisition is repeated several times, for example 1000 times, in such a way as to obtain an average spectrum $I_0$ of an electromagnetic radiation emitted by the emitter 10. Each spectrum acquired in the absence of an object between the emitter 10 and the detector 12, then digitized by the converter 18, is a histogram indicating a number of photons received at each energy, in a predetermined discrete energy range, for example between 0 and 150 keV.

These spectrums are averaged over a large number of acquisitions in order to minimize the effect of the photon noise. A threshold value can then be imposed in terms of average number of photons received at each energy, for example 5, below which the values of this average spectrum $I_0$ are not taken into account. The average emission spectrum $I_0$ is therefore finally retained in at least one energy band, referred to as an emission band $B_0$. In this emission band $B_0$, note in particular that there are no zero values of the average spectrum $I_0$, which is important in order to be able to calculate the comparison functions of the reference objects and of the materials to be identified.

Note that the successive acquisitions are carried out by the detector 12, for example on the command from the calculator 20, while the calculations of the average spectrum $I_0$ and of the emission band $B_0$ are carried out thanks to an execution of the program 28 by the processor 22.

Starting from the following step 102, the calibration method is applied for each reference object of which the material and the thickness is known. For a reference object Mref of known material and thickness, the step 102 consists in acquiring, as in the step 100, several spectrums, for example 1000, in such a way as to obtain an average spectrum I of an electromagnetic radiation transmitted by the reference object Mref. As previously, each spectrum acquired in the presence of the reference object Mref, then digitized by the converter 18, is a histogram indicating a number of photons received at each energy, in the same predetermined discrete energy range.

These spectrums are averaged over a large number of acquisitions in order to again minimize the effect of the photon noise. A threshold value can then be imposed in terms of average number of photons received at each energy, for example 5, below which the values of this average spectrum I are not taken into account. The average spectrum I is therefore finally retained in at least one energy band, referred to as a transmission band B. In this transmission band B, also note that there are no zero values of the average spectrum I, which is preferable because not measuring any photon transmitted in a given channel does not bring any pertinent information on the object considered: at most this means that the object is sufficiently attenuating in this energy channel to absorb all of the photons.

Note likewise that the successive acquisitions are carried out by the detector 12, for example on the command from the calculator 20, while the calculations of the average spectrum I and of the transmission band B are carried out thanks to an execution of the program 28 by the processor 22.

During a step 104, carried out on the execution of the program 28, the intersection between the emission band $B_0$ and the transmission band B for the reference object Mref is determined. It defines the reference band B(Mref) for the reference object Mref. This reference band is constituted of a plurality of channels, with each channel corresponding to an energy range. In particular, an energy range can be represented by a discrete energy value of the discrete energy range of the spectrums supplied by the converter 18.

Then, during a step 106 of establishing of a comparison function, carried out on the execution of the program 28, at each discrete energy value for which the calculation can be carried out in the reference band and for each spectrum acquired in the step 102, a comparison coefficient calculation is carried out, for example on the basis of the equation (1) (transmission coefficient) or of the equation (2) (attenuation coefficient). As such as many comparison functions as spectrums measured are obtained.

Finally, during a last step 108, carried out on the execution of the program 28, the reference spectral parameters are determined using previously established comparison functions, then stored in the database 26.

According to a first possible embodiment, the reference spectral parameters are spectral coefficients obtained, in each channel of the reference band, by averaging the values of the previously established comparison functions. In other words, a statistical average is carried out on each comparison function, and the spectral coefficients are determined using values, in different energy channels, of this comparison function. As such, in practice, at each discrete energy value in the reference band B(Mref) of the reference object considered, the average of all of the corresponding comparison coefficients calculated in the step 106 is retained as the reference spectral coefficient for the channel corresponding to this discrete energy. As such, if the reference band B(Mref) comprises N(Mref) channels, i.e. in fact N(Mref) discrete energy values, N(Mref) reference spectral coefficients are calculated and recorded in the database 26 for the reference object Mref. Note that since the comparison coefficients may not have all been able to be calculated in the step 106, due to the possible absence of photons measured for certain acquisitions at certain energies, the average values that the reference spectral coefficients constitute are not all calculated over the same number of values, but this does not cause any particular problem, other than a possible slight bias largely attenuated by the number of acquisitions. Furthermore, optionally, it is also possible to not take into account zero value coefficients in the calculation of the averages, if it is desired to consider that these zero values (no photon measured in the corresponding channel) are not significant.

As indicated previously, according to other possible embodiments, the reference spectral parameters of the reference object Mref can be statistical parameters, in particular parameters of a probability density allowing for the calculation of a probability of measuring spectral coefficients in the presence of the reference object Mref in its reference band B(Mref). By way of a non-restricted example, on the basis of a multivariate normal distribution model of dimension N(Mref) able to be simplified as N(Mref) independent normal distributions each operating in one of the channels of the reference band B(Mref) for the statistical modeling of the corresponding reference spectral coefficient, the reference spectral parameters are obtained, in each channel of the reference band, by establishing:

the average of the values of the previously established comparison functions (by possibly excluding the zero values), and the standard deviation of the values of the previously established comparison functions (by possibly excluding the zero values).

As such, N(Mref) reference spectral averages and N(Mref) reference spectral standard deviations are calculated and recorded in the database 26 for the reference object Mref.

The calibration method detailed hereinabove can be executed for p different reference materials and, for each of these p reference materials, for a variable number of reference thicknesses. By way of example, in an application for detecting plastic materials, p=3 different reference materials can be used, i.e. Polyethylene (PE), Polyoxymethylene (POM) and Polyvinylidene fluoride (PVDF), and, for each of these three materials, 50 thicknesses varying from 1 to 50 mm in 1 mm steps. A database 26 of reference spectral parameters relating to 150 reference objects is as such obtained.

Identification of an Unknown Material

The method for identifying an unknown material M shall now be described in detail in reference to the FIG. 3. It consists for example in determining its nature and its thickness from a comparison of the spectral coefficients coming from a measurement of this material with the aforementioned reference spectral parameters. In a particularly simple embodiment and according to the database example hereinabove, it could be limited to selecting, among the 150 reference objects of which the reference spectral parameters are recorded in the database 26, the one that corresponds the best to the measurements carried out on the material M. But optionally and in a finer embodiment, one can proceed with an interpolation of the aforementioned reference spectral parameters, making it possible to finally select intermediate thicknesses for greater precision for the identification. As such, the universe of possible results for the identification of the unknown material M is more substantial than the set of 150 reference objects.

During a first step of measuring 200 of the method for identifying, a material to be identified M is placed between the emitter 10 and the detector 12. As for the steps 100 and 102, at least one spectrum is obtained at the output of the converter 18, in the form of a histogram indicating a number of photons received at each energy, in the predetermined discrete energy range. If the target application imposes a rapid measurement, a single spectrum is acquired. Otherwise, several spectrums can be acquired and averaged in order to reduce the impact of the photon noise on the measurement.

Here again, a threshold value can be imposed in terms of number of photons received at each energy, for example 5, below which the values of the measured spectrum are not taken into account. The measured spectrum is therefore defined in at least one energy band wherein its values are greater than or equal to the threshold value. During a step 202, this energy band is compared to the emission band $B_0$ and their intersection is then determined, defining as such a measurement band Bm.

At each discrete energy value of this measurement band Bm, i.e. for each of its channels, a spectral coefficient can be determined (step 204) according to the equation (1) (transmission coefficient) or the equation (2) (attenuation coefficient) in order to obtain a comparison function linked to the material to be identified M.

Note that the acquisition of a spectrum is carried out by the detector 12, for example on the command from the calculator 20, while the calculation of a possible average spectrum, where applicable, of the measurement band Bm and of the spectral coefficients determined in the step 204 are carried out thanks to an execution of the program 30 by the processor 22.

For the rest of the identification of the unknown material M, the spectral coefficients determined in the step 204 are compared with the reference spectral parameters stored in the database 26. This comparison is, as already mentioned previously, either a direct comparison if the coefficients determined in the step 204 and the reference spectral parameters are of a comparable nature, or for example a maximization of probability density or probabilities calculated via Bayesian inference if the reference spectral parameters are more complex statistical parameters. More generally, this comparison comprises the optimization of a cost function (distance, probability density, probability, etc.) that is configured, for each reference object Mref, using the corresponding reference spectral parameters and to which are applied the values of the spectral coefficients determined in the step 204.

According to a preferred embodiment shown in the FIG. 3, adapted in particular when the reference objects are of several different materials and of several different thicknesses for each material:

in a first phase PH1 including steps $206_i$ to $218_i$, executed independently for each reference material, an optimum thickness (in the sense of an optimization of the cost function) is determined for each reference material, according to a method in at least two steps each including a comparison of the spectral coefficients determined in the step 204 with a portion of the reference spectral parameters, in a second phase PH2 including steps 220 and 222, an optimum thickness, among all of the optimum thicknesses determined in the first phase, is selected on the basis of an optimization of a criterion evaluated in at least one energy band that is common to the set of energy bands wherein the optimum thicknesses were determined.

In the rest of the description of the first phase PH1, only the steps $206_1$ to $218_1$ are detailed, relative to a first material M1 for which N1 reference objects of different thicknesses are identified in the database 26. The steps $206_i$ to $218_i$, for $2 \leq i \leq p$ are executed in the same way for any material Mi for which Ni reference objects of different thicknesses are identified in the database 26.

During a first step $206_1$ of the first phase applying to the N1 reference objects made of material M1 of the database 26, carried out on the execution of the program 32, the measurement band Bm is compared to each of the reference bands $B_{1,1}, \ldots B_{1, N1}$ associated with these N1 reference objects. An energy band $NE_{1,i}$ that is common to all of these reference bands and to the measurement band, more precisely the intersection of the energy bands $B_{1,1}, \ldots B_{1, N1}$ and Bm, is determined using these comparisons.

Figure 4:
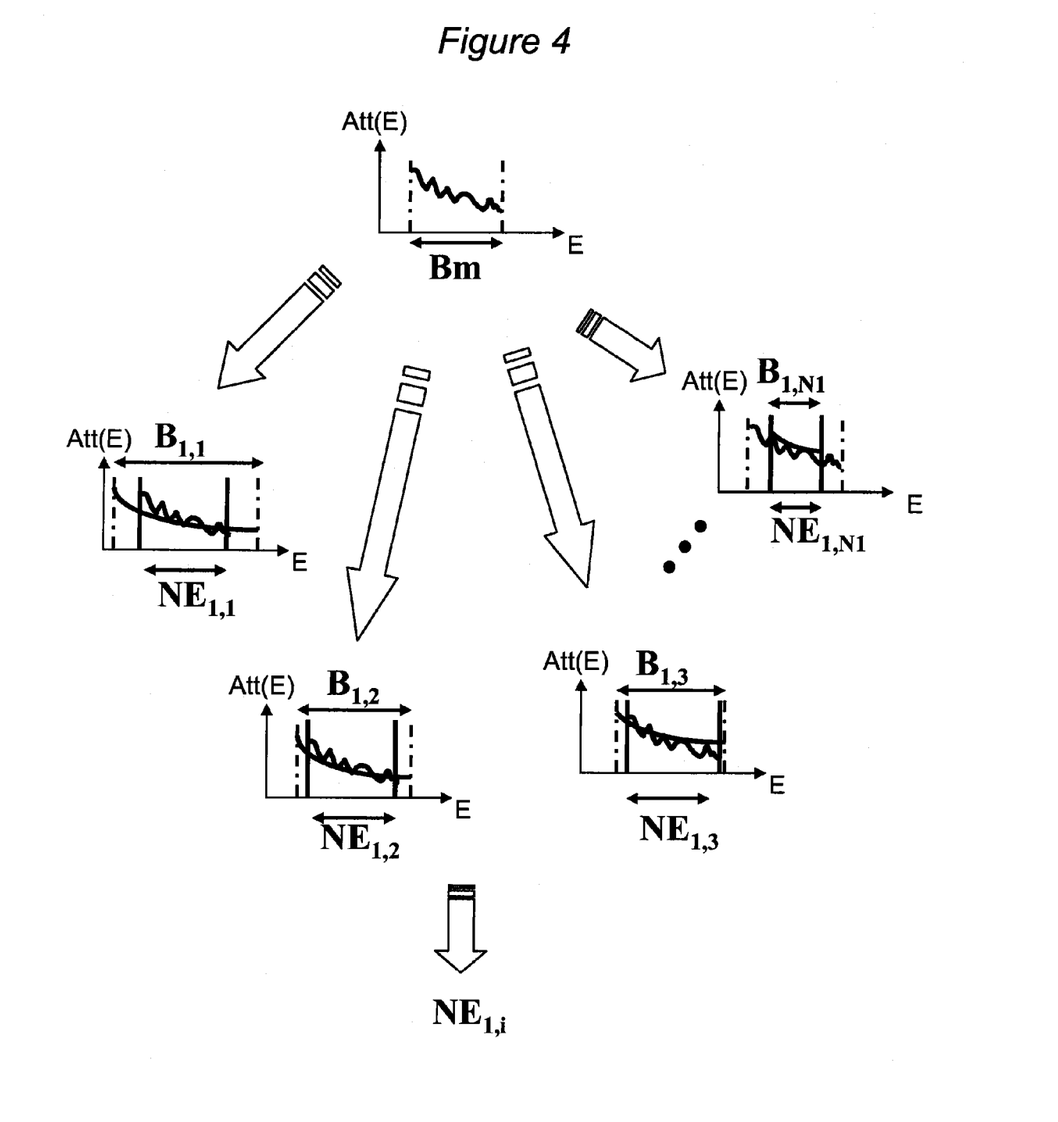
FIGS. 4 and 5 show the respective operations of certain steps of the method for identifying of FIG. 3.

As is more precisely shown in FIG. 4, this determining of the shared energy band $NE_{1,i}$ can be carried out in two steps. A first step consists in successively comparing the measurement band Bm with each of the reference bands $B_{1,1}, \ldots B_{1, N1}$ in order to determine therein the respective intersections $NE_{1,1}, \ldots NE_{1, N1}$. Then these respective intersections are compared with one another so that the one that has the least channels (i.e. the least discrete energies) $NE_{1,i}$ is selected as the shared energy band that is common to all of the reference bands $B_{1,1}, \ldots B_{1, N1}$ and to the measurement band Bm.

During a following step $208_1$ of the first phase PH1, carried out on the execution of the program 32, n reference objects made of material M1 are selected from among the N1 of the database 26 as possible candidates for the unknown material M. This selecting is carried by comparing the spectral coefficients determined in the step 204 with the reference spectral parameters of the N1 reference objects made of material M1 in the shared energy band $NE_{1,i}$. The n reference objects optimizing the previously mentioned cost function and defined in this shared energy band $NE_{1,i}$ are retained. In practice, n is between 2 and N1−1. In the example shown in FIG. 3, it is more precisely between 3 and N1−1.

Then, during a following step $210_1$ of the first phase PH1, carried out on a new iteration of the program 32 and applying to the n possible candidates selected during the preceding step, the measurement band Bm is compared to each of the reference bands associated with these n possible candidates. A shared energy band that is common to these n reference bands and to the measurement band Bm is determined using these comparisons. Since the number of energy bands of which the intersection is sought (n+1) is less than that (N1+1) of the step $206_1$, the shared energy band determined in this step necessarily includes the shared energy band determined in the step $206_1$.

As in step $206_1$, this step is followed by a new step of selecting similar to the step $208_1$. During this new selection, n' reference objects made of material M1 are selected from among the n possible candidates as new possible candidates for the unknown material M. This selection is carried out by comparing the spectral coefficients determined in the step 204 with the reference spectral parameters of the n possible candidates in the shared energy band determined in the step $210_1$. The n' reference objects, among the n possible candidates, optimizing the previously mentioned cost function and defined in this new shared energy band are retained. In practice n' is at most equal to n−1.

The program 32 is iterated as many times as desired, possible and necessary in order to finally reach a step $212_1$ of selecting two reference objects made of material M1 among the last possible candidates selected in the preceding step of selecting. During this step of selecting $212_1$, two reference objects made of material M1 are selected as new possible candidates for the unknown material M. This selection is carried out by comparing the spectral coefficients determined in the step 204 with the reference spectral parameters of the last possible candidates retained in the previous step of selecting in the shared energy band that is common to the measurement band and to the energy bands of these last possible candidates. The two reference objects, among the last possible candidates, optimizing the previously mentioned cost function and defined in this new shared energy band are retained. Note that the step $212_1$ is the step that necessarily directly follows the step $210_1$ if n=3. Note also that the shared energy band wherein is carried out this last step of selecting includes the previously determined shared energy band, which itself includes the shared energy band determined before, and so on. In this way, it is clear that the more precise the selection becomes, the more the shared energy band wherein this selection is carried out is large and the more reliable the selection becomes.

Alternatively, in a particularly simple embodiment, the step of selecting $212_1$ could consist in a selection of a single reference object among the last possible candidates, which would end the first phase PH1 of the method for identifying for the material M1.

But optionally and in a finer embodiment, the step of selecting $212_1$ selects two reference objects made of material M1 among the last possible candidates so that it can be followed by an interpolation between these two reference objects and by one last finer selection. Note that, since realistically a single thickness of material M1 has to optimize the previously mentioned cost function, the two reference objects made of material M1 selected are of successive thicknesses in the database 26. Note finally moreover that in the particular case (not shown) where n would be equal to 2 in the step $208_1$, the iterations $210_1, \ldots, 212_1$ would be suppressed and it is the step $208_1$ itself that would be followed by an interpolation between these two reference objects and by one last finer selection.

During a step $214_1$ preceding the interpolation $216_1$ and carried out on the execution of the program 34, the measurement band Bm is compared to each of the reference bands associated with the two reference objects selected among the last possible candidates. A shared energy band that is common to these two reference bands and to the measurement band Bm, more precisely the intersection of these three energy bands, is determined using these comparisons.

Figure 5:
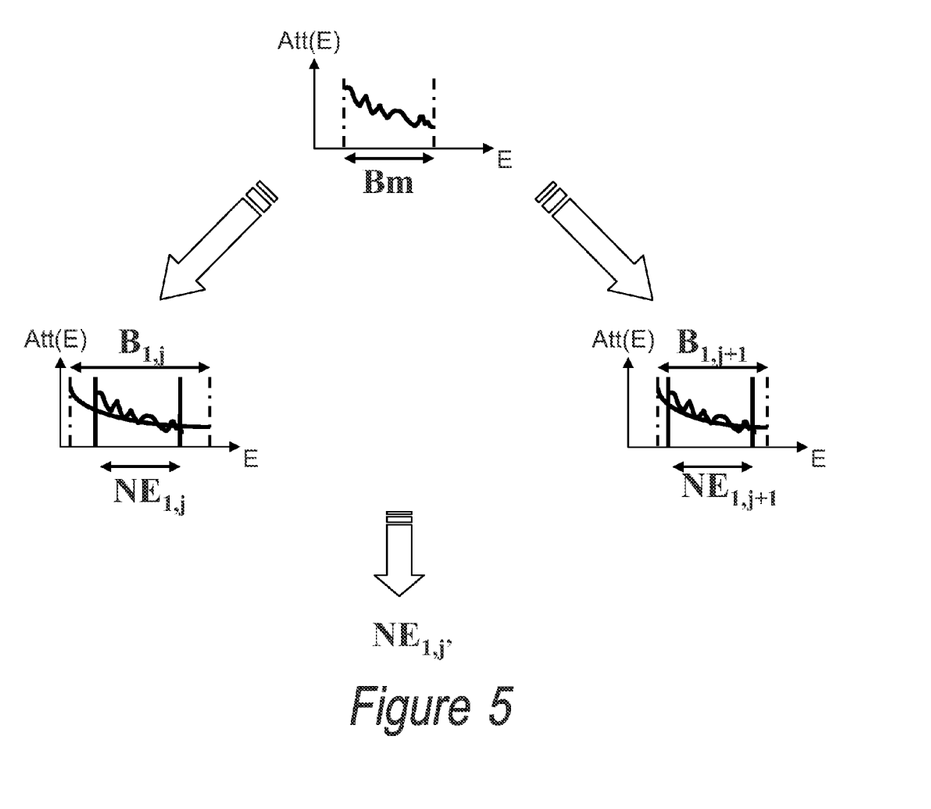

As is more precisely shown in FIG. 5, this determination of the shared energy band can be carried out in two steps. A first step consists in successively comparing the measurement band Bm with each of the reference bands $B_{1,j}$ and $B_{1,j+1}$ of the two reference objects of successive thicknesses selected in order to determine the respective intersections $NE_{1,j}$ and $NE_{1,j+1}$. Then these respective intersections are compared with one another so that the one that has the least channels (i.e. the least discrete energies) $NE_{1,j'}$ is selected as the energy band that is common to the reference bands $B_{1,j}$ and $B_{1,j+1}$ and to the measurement band Bm.

The interpolation $216_1$ consists in applying an interpolation of the reference spectral parameters of the two reference objects of successive thicknesses selected in the shared energy band $NE_{1,j'}$. This interpolation is carried out independently in each channel, i.e. in the example considered for each discrete energy of the shared energy band $NE_{1,j'}$. This concerns in fact estimating additional reference spectral parameters assumed to be relative to virtual additional reference objects of thicknesses between the two successive thicknesses of the two reference objects selected. A way that is very simple and well know to proceed with such an interpolation is to choose a discretization step in thickness, for example $1/N^{th}$ of the difference between the two successive thicknesses of the two reference objects selected (N=20 for example), then to interpolate linearly each of the reference spectral parameters in each channel by application of a barycentric linear combination of the corresponding parameters of the two reference objects selected. N+1 reference objects are thus obtained made of material M1 of N+1 different successive thicknesses, more precisely the two reference objects selected and the N−1 interpolated virtual additional reference objects.

This step of interpolating $216_1$ is followed by a step $218_1$ of selecting a single reference object made of material M1 among the N+1 possible reference objects. This selecting is carried out by comparing the spectral coefficients determined in the step 204 with the reference spectral parameters of these N+1 possible reference objects in the shared energy band $NE_{1,j'}$ determined in the step $214_1$. The reference object, which can in particular be virtual, among the N+1 possible objects, optimizing the previously mentioned cost function and defined in the shared energy band $NE_{1,j'}$ is retained. This step $218_1$ terminates the first phase PH1 of the method for identifying by the selecting of an optimum thickness E1 for the reference material M1.

As indicated previously, one proceeds likewise for each reference material Mi, 2≤i≤p, during similar steps $206_i$ to $218_i$ executed independently for each reference material. At the end of the first phase PH1, a selection of p thicknesses E1, . . . , Ep is obtained, optimal respectively for the p reference materials M1, . . . , Mp, i.e. having optimized cost functions in steps $218_1, \ldots, 218_p$ in respectively p shared energy bands $NE_{1,j'}, \ldots, NE_{p,j'}$ determined respectively in the steps $214_1, \ldots, 214_p$.

The second phase PH2, carried out by execution of the program 34, comprises a step 220 of determining an energy band that is common to the p shared energy bands $NE_{1,j'}, \ldots, NE_{p,j'}$ determined respectively in the steps $214_1, \ldots, 214_p$. More precisely, this step 220 determines the intersection of the p shared energy bands $NE_{1,j'}, \ldots, NE_{p,j'}$. This intersection is noted NE.

Finally, the second phase PH2 comprises a step 222 of the final selection of a single optimum thickness associated with a reference material among the p optimum thicknesses E1, . . . , Ep. This selection is carried out by comparing the spectral coefficients determined in the step 204 with the reference spectral parameters of these p reference objects, real or virtual, corresponding to the p optimum thicknesses E1, . . . , Ep in the shared energy band NE. Possibly, if the calculation of the optimizations of the cost functions can be separated one channel from the other in the shared energy band NE, the results of the steps $218_1, \ldots, 218_p$ can be exploited in this step 222 in order to limit the complexity of the calculation. The reference material Mk and its associated optimum thickness Ek, among the p reference objects, real or virtual, corresponding to the p optimum thicknesses E1, . . . , Ep, optimizing the previously mentioned cost function and defined in the shared energy band NE, are retained.

The unknown material M is therefore identified as being made of material Mk and of thickness Ek.

It clearly appears that a method for identifying material such as that described previously makes it possible to progressively refine the selection by increasing at the same time the shared energy band that is common to the reference spectral parameters taken into account and to the spectral coefficients coming from the measurement. The increase in the shared energy band in the flow of the selection makes it possible to improve the reliability of it and to finally obtain a more precise identification.

Many other alternative embodiments of the invention than those previously considered can also be imagined by retaining this advantageous property.

Figure 6:
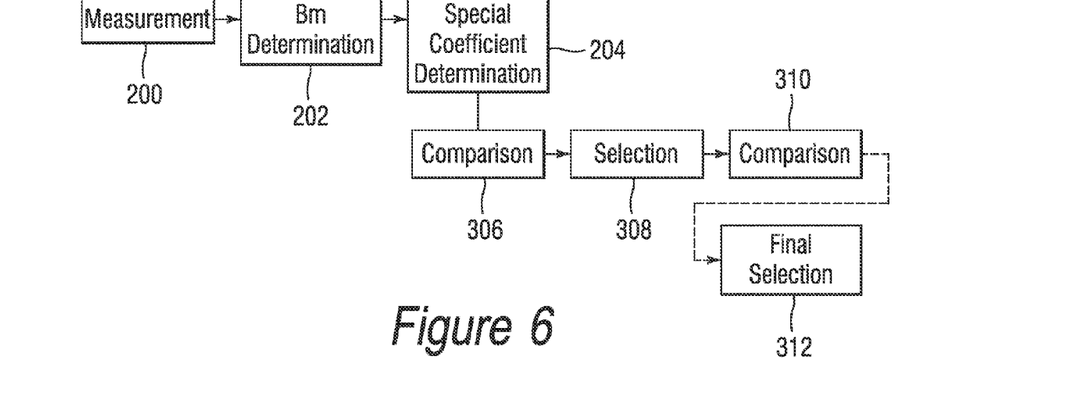
FIG. 6 shows the successive steps of a method for identifying according to a second embodiment of the invention.

In particular, in accordance with another simpler embodiment shown in FIG. 6, it is not always necessary to proceed in two phases PH1 and PH2 such as mentioned in the example shown in FIG. 3. The reference objects for which reference spectral parameters are available are not necessarily classed by nature, by thickness or according to other criteria. They can be considered in their entirety as N reference objects to which the material to be identified M has to be compared in order to be identified.

According to this other embodiment, the step 204 is followed by a step 306 during which the measurement band Bm is compared to all of the reference bands of the N reference objects. An energy band that is common to all of these reference bands and to the measurement band, more precisely the intersection of all of the reference bands and of the measurement band, is determined using these comparisons.

The step 306 is followed by a step 308 during which n possible candidates are selected from among the N reference objects. The value of n can be chosen freely between 2 and N−1. This selection is carried out by comparing the spectral coefficients determined in the step 204 with the reference spectral parameters of the N reference objects in the shared energy band determined in the step 306.

Then, during a step 310, the measurement band Bm is compared to each of the reference bands associated with the n possible candidates. An energy band that is common to these n reference bands and to the measurement band Bm is determined using these comparisons. Since the number of energy bands of which the intersection is sought is less than that of the step 306, the shared energy band determined in this step necessarily includes the shared energy band determined in the step 306.

Either directly following the step 310, or after several iterations of successive selections (during which the selection of possible candidates is reduced to successively n', n", ... with N>n>n'>n" ... ), movement passes finally to a step 312 during which a single reference object is selected among the n (or n', n", ... in case of successive selections) possible candidates. This selection is carried out by comparing the spectral coefficients determined in the step 204 with the reference spectral parameters of the n (or n', n", ... in case of successive selections) possible candidates in the energy band that is common to the measurement band and to the reference bands of the possible candidates. The unknown material M is then identified as being identical to the reference object finally selected.

Finally note that each time an energy band is involved, whether it be the measurement band, the reference bands, or the shared energy bands, such an energy band is not necessarily continuous: its can be constituted of several separated energy bands.

Comparing Coefficients Coming from the Measurement with the Reference Spectral Parameters The forms that the comparisons may take between spectral coefficients coming from the measurement of the material to be identified M and reference spectral parameters in a given energy band with NE channels shall now be specified, according to different possible embodiments. These comparisons are those that were mentioned in steps $208_1 \ldots 208_p$, $212_1 \ldots 212_p$, $218_1 \ldots 218_p$, 308 and 312.

As indicated previously, according to a possible embodiment, the reference spectral parameters can be spectral coefficients that can be compared directly with spectral coefficients measured for the unknown material M. Noting $CM=(CM_1, \ldots, CM_{NE})$ the spectral coefficients coming from the measurement of the unknown material M and $CR=(CR_1, \ldots, CR_{NE})$ the reference spectral coefficients of any one of the reference objects, the cost function can be defined as a distance d to be minimized, taking the following form:

$$d(CM, CR) = \sqrt{(CM_1-CR_1)^2 + \ldots + (CM_{NE}-CR_{NE})^2},$$ the values $CM_i$ and $CR_i$, $1 \leq i \leq NE$, being scalars.

It can also be, more simply, a pseudo distance:

$$d'(CM,CR) = (CM_1-CR_1)^2 + \ldots + (CM_{NE}-CR_{NE})^2.$$

Note that the calculations $(CM_1-CR_1)^2, \ldots, (CM_{NE}-CR_{NE})^2$ of these cost functions can be separated one channel from the other (it is sufficient to add them together) in such a way that when they are implemented in the aforementioned steps $218_1, \ldots, 218_p$, they can be judiciously retained in memory, for example in vector form, in order to then be exploited in step 222 since the shared energy band considered during this step is the intersection of the shared energy bands considered in the steps $214_1, \ldots, 214_p$. This avoids additional calculations.

As indicated previously, according to another possible embodiment, the reference spectral parameters can be statistical parameters, in particular probability density parameters. By way of a non-restricted example, on the basis of a multivariate normal distribution model of dimension NE able to be simplified, by taking an assumption of independence of the NE channels, as NE independent normal distributions each operating in one of the channels of the given energy band, note respectively $\mu R=(\mu R_1, \ldots, \mu R_{NE})$ and $\sigma R=(\sigma R_1, \ldots, \sigma R_{NE})$ the "average" and "standard deviation" reference spectral parameters of any one of the reference objects. The cost function can then be defined as a probability density to be maximized, taking the following form:

$$f_{\mu R, \sigma R}(CM) = \prod_{i=1}^{NE} \frac{1}{\sqrt{2\pi}\, \sigma R_i} \cdot \exp\left[-\frac{1}{2}\left(\frac{CM_i - \mu R_i}{\sigma R_i}\right)^2\right].$$

Also note here that the calculations $$\frac{1}{\sqrt{2\pi}\, \sigma R_1} \cdot \exp\left[-\frac{1}{2}\left(\frac{CM_1 - \mu R_1}{\sigma R_1}\right)^2\right], \ldots,$$

$$\frac{1}{\sqrt{2\pi}\, \sigma R_{NE}} \cdot \exp\left[-\frac{1}{2}\left(\frac{CM_{NE} - \mu R_{NE}}{\sigma R_{NE}}\right)^2\right]$$

of this cost function can be separated one channel from the other (it is sufficient to multiply them together) in such a way that when they are implemented in the aforementioned steps $218_1, \ldots, 218_p$, they can be judiciously retained in memory, for example in vector form, in order to then be exploited in step 222 since the shared energy band considered during this step is the intersection of the shared energy bands considered in the steps $214_1, \ldots, 214_p$. This avoids additional calculations.

Of course, it is also possible to take a more complex multivariate normal distribution model, i.e. not assuming that the channels are independent among themselves. In this case, the cost function takes a more complex form that includes the taking into account of the more general form of a covariance matrix. As this more complex form and the covariance calculations are well known, details shall not be provided here. It is also possible to select statistical models other than normal distributions.

In this other embodiment, the cost function can also take a form other than a probability density to be maximized: for example a directly calculated conditional probability and to be maximized also. More precisely, this conditional probability is the conditional posterior probability, noted as $p_{CM}[(\mu R, \sigma R)]$, that the material to be identified M is that corresponding to the reference spectral parameters $(\mu R, \sigma R)$ knowing the value CM of the spectral coefficients coming from the measurement.

According to Bayes' theorem this probability can be broken down as follows:

$$p_{CM}[(\mu R, \sigma R)] = p_{\mu R, \sigma R}(CM) \cdot \frac{p[(\mu R, \sigma R)]}{p(CM)}, \quad (3)$$

where $p_{\mu R, \sigma R}(CM)$ is the conditional posterior probability of obtaining a value CM of spectral coefficients coming from the measurement for the reference object of reference spectral parameters ($\mu R$, $\sigma R$), $p[(\mu R, \sigma R)]$ is the prior probability of being in the presence of the reference object of reference spectral parameters ($\mu R$, $\sigma R$) and $p(CM)$ is the prior probability of the value CM of spectral coefficients coming from the measurement.

By way of a non-restricted example, as previously, on the basis of a multivariate normal distribution model of dimension NE able to be simplified, taking an assumption of independence of the NE channels, as NE independent normal distributions each operating in one of the channels of the given energy band, note $\mu R = (\mu R_1, \ldots, \mu R_{NE})$ and $\sigma R = (\sigma R_1, \ldots, \sigma R_{NE})$ respectively the "average" and "standard deviation" reference spectral parameters of any of the reference objects. Moreover, noting p as the number of reference materials and Nk the number of reference thicknesses for the k-th reference material (the universe of the reference thicknesses then comprises not only those for which a calibration has been carried out, but in addition those for which the reference spectral parameters were obtained via interpolation), it is possible to explain each of the right-hand side terms of the equation (3).

Therefore, $$p[(\mu R, \sigma R)] = \frac{1}{p} \cdot \frac{1}{Nk}, \quad (4)$$

where k designates the material of the reference object of reference spectral parameters ($\mu R$, $\sigma R$).

Also, $$p_{\mu R, \sigma R}(CM) = \prod_{i=1}^{NE} p_{\mu R_i, \sigma R_i}(CM_i)$$

through independence of the channels.

Moreover, for any i, by closely approaching the value of $CM_i$ between a lower limit $Inf(CM_i)$ and an upper limit $Sup(CM_i)$, the following can be written:
$p_{\mu R_i, \sigma_i}(CM_i) = p_{\mu R_i, \sigma R_i}(Inf(CM_i) < CM_i < Sup(CM_i))$, or, under a normal distribution:

$$p_{\mu R_i, \sigma R_i}(CM_i) = \int_{Inf(CM_i)}^{Sup(CM_i)} \frac{1}{\sqrt{2\pi} \, \sigma R_i} \cdot \exp\left[-\frac{1}{2}\left(\frac{x - \mu R_i}{\sigma R_i}\right)^2\right] dx.$$

The following expression results:

$$p_{\mu R, \sigma R}(CM) = \prod_{i=1}^{NE} \int_{Inf(CM_i)}^{Sup(CM_i)} \frac{1}{\sqrt{2\pi} \, \sigma R_i} \cdot \exp\left[-\frac{1}{2}\left(\frac{x - \mu R_i}{\sigma R_i}\right)^2\right] dx. \quad (5)$$

For any i, since the value of $CM_i$ depends on the comparison function chosen, then the values of $Inf(CM_i)$ and $Sup(CM_i)$ are also dependent on it.

For example, if the comparison function takes the form of a transmission function, the value of $CM_i$ is $$CM_i = \frac{I(i)}{I_0(i)},$$

where $I(i)$ and $I_0(i)$ designate respectively the measurement of the number of photons transmitted by the material to be identified and that of the number of incident photons in the i-th canal.

Now, the number $I(i)$ can be closely approached by:

$$I(i) - 1 < I(i) < I(i) + 1,$$

or $$\frac{I(i) - 1}{I_0(i)} < \frac{I(i)}{I_0(i)} < \frac{I(i) + 1}{I_0(i)}.$$

Giving, in the case of a transmission function:

$$Inf(CM_i) = \frac{I(i) - 1}{I_0(i)}$$

and $$Sup(CM_i) = \frac{I(i) + 1}{I_0(i)}.$$

If the comparison function takes the form of an attenuation function, through a similar calculation $$Inf(CM_i) = -\ln\left(\frac{I(i) + 1}{I_0(i)}\right)$$

and $$Sup(CM_i) = -\ln\left(\frac{I(i) - 1}{I_0(i)}\right)$$

are obtained.

Finally, the last term of the equation (3) can be explained in the following way, by development using the law of total probability over all of the reference objects in all of the universe of reference thicknesses:

$$p(CM) = \frac{1}{p} \cdot \sum_l \frac{1}{Nl} \cdot \sum_{j=1}^{Nl} p_{\mu R(l,j), \sigma R(l,j)}(CM)$$

$$= \frac{1}{p} \cdot \sum_l \frac{1}{Nl} \cdot \sum_{j=1}^{Nl} \prod_{i=1}^{NE} p_{\mu T(l,j)_i, \sigma R(l,j)_i}(CM_i).$$

Under a multivariate normal distribution, the following expression results:

$$p(CM) = \frac{1}{p} \cdot \sum_l \frac{1}{Nl}. \quad (6)$$

-continued $$\sum_{j=1}^{Nl} \prod_{i=1}^{NE} \int_{Inf(CM_i)}^{Sup(CM_i)} \frac{1}{\sqrt{2\pi}\,\sigma R(l,j)_i} \cdot \exp\left[-\frac{1}{2}\left(\frac{x-\mu R(l,j)_i}{\sigma R(l,j)_i}\right)^2\right] dx.$$

By transferring equations (4), (5) and (6) into the equation (3), the following expression (7) is finally obtained:

$$p_{CM}[(\mu R, \sigma R)] = \frac{1}{Nk} \cdot \frac{\prod_{i=1}^{NE} \int_{Inf(CM_i)}^{Sup(CM_i)} \frac{1}{\sqrt{2\pi}\,\sigma R_i} \cdot \exp\left[-\frac{1}{2}\left(\frac{x-\mu R_i}{\sigma R_i}\right)^2\right] dx}{\sum_{l} \frac{1}{Nl} \cdot \sum_{j=1}^{Nl} \prod_{i=1}^{NE} \int_{Inf(CM_i)}^{Sup(CM_i)} \frac{1}{\sqrt{2\pi}\,\sigma R(l,j)_i} \cdot \exp\left[-\frac{1}{2}\left(\frac{x-\mu R(l,j)_i}{\sigma R(l,j)_i}\right)^2\right] dx}.$$

This expression can be simplified. Indeed, as we are seeking, in the universe of possible reference objects (including for the interpolated reference thicknesses), the one that maximizes the probability $p_{CM}[(\mu R, \sigma R)]$, it is sufficient to know the latter to within a constant. Yet prior probability p(CM) is independent of the reference objects, consequently it constitutes simply a normalization factor at 1 in the equation (3). It is therefore not useful to calculate it, which substantially simplifies the expression (7).

Moreover, a change in variable can be carried out in the equation (5) in such a way as to express using the Gauss error special function erf which is well known. More precisely, it can be noted that:

$$\int_{Inf(CM_i)}^{Sup(CM_i)} \frac{1}{\sqrt{2\pi}\,\sigma R_i} \cdot \exp\left[-\frac{1}{2}\left(\frac{x-\mu R_i}{\sigma R_i}\right)^2\right] dx =$$
$$\frac{1}{2} \cdot \left(1 + \text{erf}\left(\frac{Sup(CM_i) - \mu R_i}{2 \cdot \sigma R_i}\right)\right) - \frac{1}{2} \cdot \left(1 + \text{erf}\left(\frac{Inf(CM_i) - \mu R_i}{2 \cdot \sigma R_i}\right)\right)$$

The expression (7) is therefore simplified as follows to provide an expression that can be easily calculated for the cost function:

$$p_{CM}[(\mu R, \sigma R)] \propto \frac{1}{Nk} \cdot \prod_{i=1}^{NE} \left[\text{erf}\left(\frac{Sup(CM_i) - \mu R_i}{2 \cdot \sigma R_i}\right) - \text{erf}\left(\frac{Inf(CM_i) - \mu R_i}{2 \cdot \sigma R_i}\right)\right].$$

An advantage of this cost function is to be normalized (to within a constant). Furthermore, as with the two preceding cost functions, its calculations $$\left[\text{erf}\left(\frac{Sup(CM_i) - \mu R_i}{2 \cdot \sigma R_i}\right) - \text{erf}\left(\frac{Inf(CM_i) - \mu R_i}{2 \cdot \sigma R_i}\right)\right]$$

can be separated one channel from the other (it is sufficient to multiply them together) in such a way that when they are implemented in the aforementioned steps $218_1, \ldots, 218_p$, they can be judiciously retained in memory, for example in vector form, in order to then be exploited in step 222 since the shared energy band considered during this step is the intersection of the shared energy bands considered in the steps $214_1, \ldots, 214_p$. This avoids additional calculations.

Other cost functions can be used on the basis of the aforementioned reference spectral parameters.

Note that a method for identifying a material according to the invention is independent of the way of which the comparisons between spectral coefficients coming from the measurement and reference spectral parameters are carried out concretely. Thus, the aforementioned examples of comparisons are advantageously applied to a method for identifying material according to the invention, but other non-described methods could very well apply to this method. Inversely, the aforementioned examples of comparisons can apply to other methods for identifying materials than those considered previously.

Note finally that the invention is not limited to the embodiments described previously. It will appear indeed to those skilled in the art that various modifications can be made to the embodiments described hereinabove, in light of the teachings that have just been disclosed. In the claims that follow, the terms used must not be interpreted as limiting the claims to the embodiments exposed in this description, but must be interpreted in order to include therein all of the equivalents that the claims aim to cover due to their formulation and of which the prediction is within the scope of those skilled in the art by applying their general knowledge to the implementation of the teachings that have just been disclosed.

The invention claimed is:

1. A method for identifying a material by spectral analysis of electromagnetic radiation emitted through the material, comprising:
measuring a spectrum of the electromagnetic radiation emitted through the material;
determining at least one measurement energy band as a measurement band, and spectral coefficients of a comparison function in the measurement band, using the measured spectrum; and
estimating, using the determined spectral coefficients, a nature of the material and/or a thickness of the material based on a set of reference spectral parameters relating to reference materials and/or reference thicknesses of the reference materials, the reference spectral parameters being defined for each reference material and/or each reference thickness of each reference material in at least one reference energy band as a reference band, which is specific to said each reference material and/or said each reference thickness of each reference material,
wherein the estimating further comprises:
prior selection of possible candidates from the reference materials and/or from the reference thicknesses of the reference materials, from a comparison of the determined spectral coefficients with at least one portion of the set of reference spectral parameters in at least one first energy band that is common to at least part of the reference bands and to the measurement band,
determining at least one new energy band that is common to reference bands of at least one portion of the possible candidates and to the measurement band, and
estimating the nature of the material and/or the thickness of the material from a comparison of the determined spectral coefficients with reference spectral parameters of the at least one portion of the possible candidates, in the at least one new energy band that is common to the reference bands of the at least one portion of the possible candidates and to the measurement band.

2. The method for identifying a material according to claim 1, wherein the prior selection of the possible candidates is carried out:
either in at least one second energy band that is common to all of the reference bands and to the measurement band,
or in at least one third energy band that is common to a predetermined portion of the reference bands and to the measurement band.

3. The method for identifying a material according to claim 1, wherein the reference materials and/or reference thicknesses of the reference materials comprise a plurality of reference materials each with a plurality of reference thicknesses.

4. The method for identifying a material according to claim 3, wherein the estimating further comprises, executed for each reference material of the plurality of reference materials:
selecting possible candidates from the plurality of reference thicknesses for said each reference material, by comparison of the determined spectral coefficients with the reference spectral parameters in at least one fourth energy band that is common to the reference bands of each reference thickness for said each reference material and to the measurement band;
selecting two consecutive reference thicknesses for said each reference material by comparison of the determined spectral coefficients with the spectral parameters of at least one portion of the possible candidates, in at least one fifth energy band that is common to the reference bands of the at least one portion of possible candidates and to the measurement band; and
estimating an optimum thickness for said each reference material by comparison of the determined spectral coefficients with spectral parameters interpolated using spectral parameters relating to the selected two consecutive reference thicknesses, in at least one sixth energy band that is common to the reference bands of the selected two consecutive reference thicknesses and to the measurement band.

5. The method for identifying a material according to claim 4, wherein the estimating further comprises selecting an overall optimum thickness, among all of optimum thicknesses each associated with a reference material of the plurality of reference materials, on the basis of an optimization of a criterion evaluated in at least one seventh energy band that is common to all of the energy bands wherein the optimum thicknesses were estimated.

6. The method for identifying a material according to claim 1, wherein the reference spectral parameters are probability density statistical parameters, said each reference material and/or said each reference thickness being thus associated with a probability density, and further comprising calculating a probability of measuring spectral coefficients in a presence of said each reference material and/or said each reference thickness in a corresponding reference band for said each reference material and/or said each reference thickness.

7. The method for identifying a material according to claim 6, wherein the comparison of the determined spectral coefficients with the reference spectral parameters further comprises estimating a value that takes a probability density of said each reference material and/or said each reference thickness when the determined spectral coefficients are applied.

8. The method for identifying a material according to claim 6, wherein the comparison of the determined spectral coefficients with the reference spectral parameters further comprises estimating a conditional posterior probability of being in the presence of said each reference material and/or said each reference thickness knowing the determined spectral coefficients, on the basis of a product of a conditional posterior probability of measuring the determined spectral coefficients in the presence of said each reference material and/or said each reference thickness and of a prior probability of being in the presence of said each reference material and/or said each reference thickness, by application of Bayes' theorem.

9. A device for identifying a material by spectral analysis of electromagnetic radiation emitted through the material, comprising:
a transmitter of electromagnetic radiation;
a measuring device configured to measure a spectrum of the electromagnetic radiation transmitted through the material;
a calculator comprising circuitry configured to:
determine at least one measurement energy band as a measurement band, and spectral coefficients of a comparison function in the measurement band, using the measured spectrum;
estimate, using the determined spectral coefficients, a nature of the material and/or a thickness of the material based on a set of reference spectral parameters relating to reference materials and/or reference thicknesses of the reference materials, the reference spectral parameters being defined for each reference material and/or each reference thickness of each reference material in at least one reference energy band as a reference band, which is specific to said each reference material and/or said each reference thickness of each reference material;
make a prior selection of possible candidates from the reference materials and/or from the reference thicknesses of the reference materials, from a comparison of the determined spectral coefficients with at least one portion of the set of reference spectral parameters in at least one first energy band that is common to at least part of the reference bands and to the measurement band;
determine at least one new energy band that is common to reference bands of at least one portion of the possible candidates and to the measurement band; and
estimate the nature of the material and/or the thickness of the material from a comparison of the determined spectral coefficients with reference spectral parameters of the at least one portion of the possible candidates, in the at least one new energy band that is common to the reference bands of the at least one portion of the possible candidates and to the measurement band.

10. A non-transitory computer readable storage medium including a computer program stored thereon, which, when executed by a computer and/or a processor, causes the computer and/or the processor to execute the method for identifying a material according to claim 1.

11. The method according to claim 1, wherein the measurement band and the reference bands are not all identical.

12. The method according to claim 1, wherein the at least one new energy band is increased relative to the at least one first energy band.

13. The device according to claim 9, wherein the measurement band and the reference bands are not all identical.

14. The device according to claim 9, wherein the at least one new energy band is increased relative to the at least one first energy band.

* * * * *